United States Patent [19]

Garay et al.

[11] Patent Number: 4,925,446

[45] Date of Patent: May 15, 1990

[54] REMOVABLE INFLATABLE INTRAGASTROINTESTINAL DEVICE FOR DELIVERING BENEFICIAL AGENTS

[75] Inventors: Garbiel L. Garay; Kathleen M. K. Garay, both of Atherton, Calif.

[73] Assignee: Transpharm Group Inc., San Francisco, Calif.

[21] Appl. No.: 215,746

[22] Filed: Jul. 6, 1988

[51] Int. Cl.⁵ .............................................. A61M 5/00
[52] U.S. Cl. ....................................... 604/96; 604/54; 604/270; 604/891.1; 128/899
[58] Field of Search ........................... 604/54, 96–103, 604/265, 270–271, 891.1; 128/344, 897–899

[56] References Cited

U.S. PATENT DOCUMENTS

| | | | |
|---|---|---|---|
| 3,589,356 | 6/1971 | Silverman | 604/271 X |
| 3,901,232 | 8/1975 | Michaels et al. | 604/892.1 |
| 4,055,178 | 10/1977 | Harrigan | 604/890.1 |
| 4,133,315 | 1/1979 | Berman et al. | 128/303 R |
| 4,207,890 | 6/1980 | Mamajek et al. | 424/473 |
| 4,416,267 | 11/1983 | Garren et al. | 128/344 |
| 4,485,805 | 12/1984 | Foster | 128/899 |
| 4,501,264 | 2/1985 | Rockey | 128/894 |
| 4,649,043 | 3/1987 | Urquhart et al. | 424/469 |
| 4,718,894 | 1/1988 | Lazorthes | 604/93 |

*Primary Examiner*—Dalton L. Truluck
*Attorney, Agent, or Firm*—Irell & Manella

[57] ABSTRACT

A removable inflatable beneficial agent delivery device that is adapted to reside in the stomach for a prolonged time period. The device comprises (1) an inflatable member which in its deflated state can be inserted into the stomach via a naso-gastric tube and which in its inflated state resides comfortably in the stomach but cannot pass through the pyloric sphincter, (2) an inflation tube connected to the inflatable member by which the inflatable member can be inflated from outside the body and which is dropped into the stomach after inflation, and (3) one or more agent-containing cartridges that are carried exteriorly on the inflatable member or the inflation tube and are capable of delivering agent to the gastrointestinal tract over a prolonged time period.

9 Claims, 1 Drawing Sheet

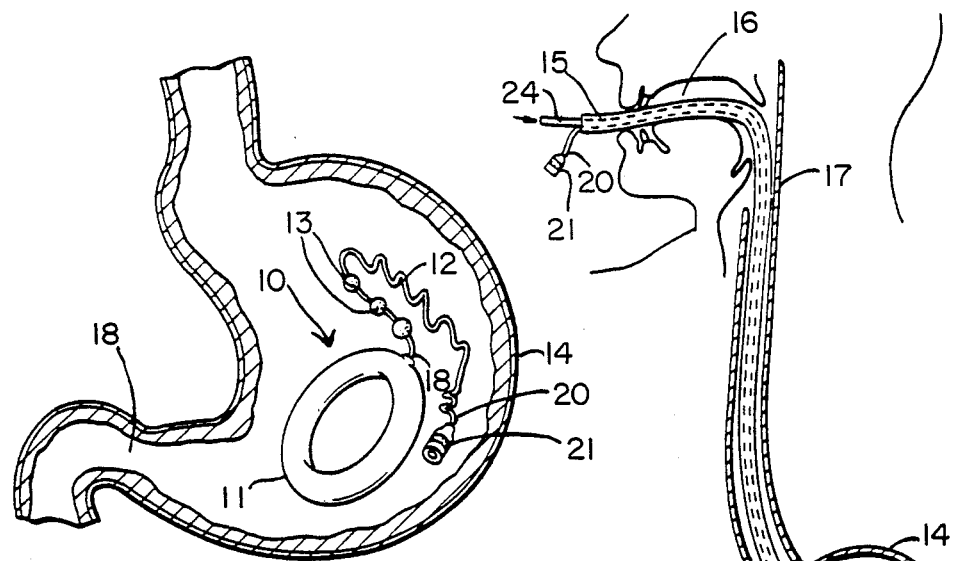
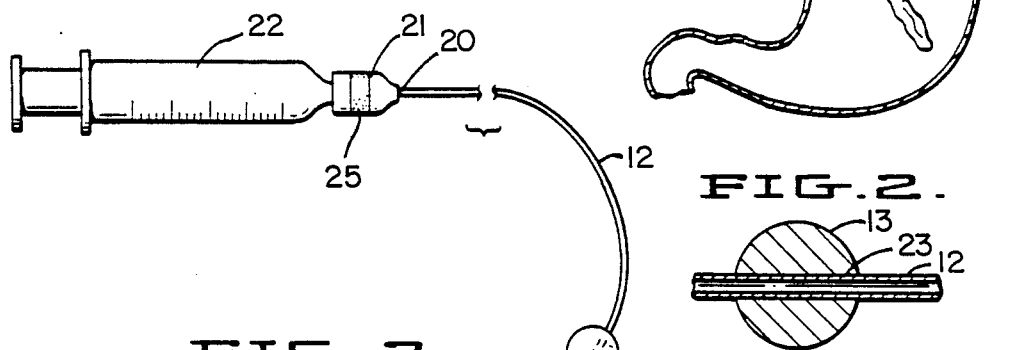
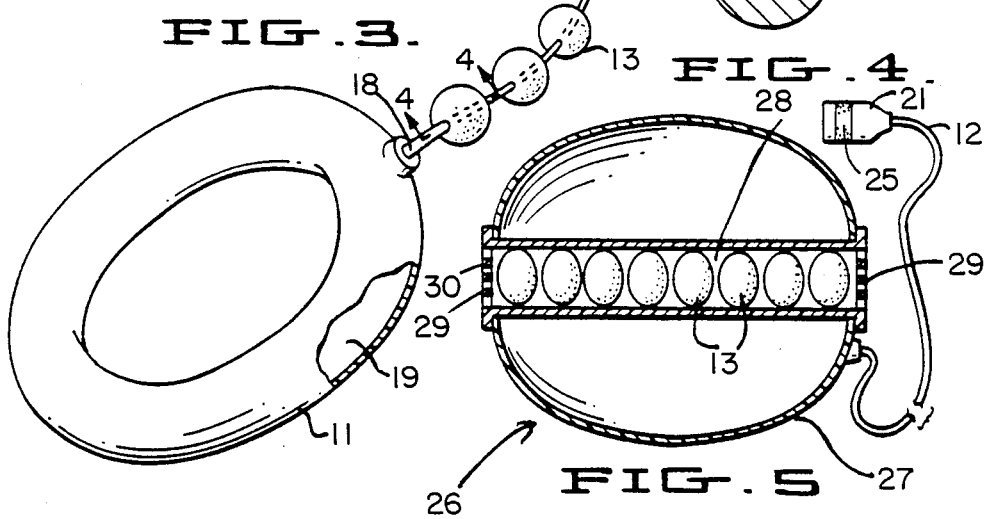

REMOVABLE INFLATABLE INTRAGASTROINTESTINAL DEVICE FOR DELIVERING BENEFICIAL AGENTS

TECHNICAL FIELD

The invention is in the field of drug delivery. More specifically it is in the field of sustained release devices for administering drugs or other beneficial agents within the gastrointestinal tract.

BACKGROUND OF THE INVENTION

The prolonged delivery of drugs orally has been a major challenge and a long desired objective in drug therapy. This is a favored route for drug administration. It is estimated that 65% of all drugs are ingested. The successful accomplishment of prolonged gastrointestinal drug delivery has great therapeutic significance in the treatment of various diseases and conditions.

Systemic and transdermal sustained drug delivery systems have been developed which are capable of delivering constant amounts of therapeutic substances from several days to several months. The major limitation to long-term oral delivery, however, is the 8–16 hour gastrointestinal transit time of an ingested substance. In order to achieve uninterrupted action for longer than 24 hours by a therapeutic substance, its passage needs to be slowed in the gastrointestinal tract or the delivery device supplying the drug has to be fixed or immobilized within the tract.

Attempts have been made either to incorporate drugs into floating devices which would empty less readily from the stomach (N. Eng. J. Med. [1981] 304:1365–1366), or to introduce balloon based devices which could be inflated by propellants or be fluid expanded in the stomach after the whole device had been swallowed. Michaels (U.S. Pat. Nos. 3,786,813; 3,788,322 and 3,901,232) proposed a series of capsular, swallowable devices. Upon ingestion, the wall of these capsules would erode, releasing a balloon support and the whole device would float in the stomach. The drug then would be released in a sustained and controlled fashion either due to the mechanical pressure exerted by a bladder on a closed drug reservoir, or dispensed from a container enclosed in a microporous membrane.

The spontaneous expulsion of such a device from the gastrointestinal tract once its active material has been expended is much more of a challenge, however. The Michaels device comes equipped with an imbedded bioerodible plug whose object is to assure the balloon's eventual deflation. In another version of the invention, the balloon loses air by being minimally permeable to a gas with which it has been inflated.

Place and Bashaw, et al disclose in U.S. Pat. Nos. 3,797,492 and 3,944,064 a variation of the system described above, suggesting that a propellant-charged capsular compartment can keep the device afloat in the stomach and also accomplish the controlled release of the active drug. Another drug-dispensing device for the prolonged administration of pharmaceuticals is disclosed in U.S. Pat. No. 4,207,890. This device is made of dual polymer envelopes, one of which swells and expands osmotically when the device reaches the stomach, while the other contains the drug and dispenses it at a predetermined determined rate based on the polymer envelope's permeability characteristics.

Yet, all these devices have major disadvantages in that they carry only a small amount of the active substance. Furthermore, as their balloon support becomes partially deflated in the stomach, this could result in their inadvertent passage into the duodenum and small intestine and produce a dangerous intestinal obstruction. Moreover, gas- or air-filled devices could burst if the individuals wearing them should travel to higher altitudes. Should the reverse occur, where an individual would travel to lower altitudes, the gas filled device could deflate.

Intragastric balloon devices have also been developed for the purpose of appetite control and weight reduction. Berman, et al (U.S. Pat. No. 4,133,315) describe a large balloon which is to be introduced deflated into the stomach via a naso-gastric tube. The balloon is to be fluid filled with an attached insufflation tube that remains in place and extends through the esophagus and the nasal passages to the outside environment. A more advanced concept of this intragastric balloon weight loss device was disclosed in U.S. Pat. No. 4,485,805. This elastomeric rubber balloon was equipped with a self-sealing valve and its inflator tube could be withdrawn from the stomach, leaving behind the fluid inflated balloon. When the desired weight loss is achieved, the balloon is to be deflated, and withdrawn from the stomach by endoscopy. Although this device was primarily developed for weight control, the inventor suggests that pharmaceuticals could also be incorporated for sustained release into the fluid used for balloon inflation.

The Garren-Edwards gastric bubble consists of a self-sealing, cylindrical intragastric balloon which has been made commercially available for weight reduction and appetite control (Endoscopy Review, 1, 57–60, 1984).

Recently, however, the phenomenon of bio or mucoadhesion with polymeric substances has received considerable attention ("Advances in Drug Delivery Systems", J. M. Anderson and S. W. Kim, Eds., Elsevier, Amsterdam, Vol. 1, 1986, pp 47–57). The temporary and adhesive attachment of prolonged release drug delivery systems to the gastrointestinal mucosa is a novel approach. However, the various mucoadhesive techniques are still under early experimental investigation.

There is clearly a need for a practical gastrointestinal drug delivery device that is relatively simple, safe to use, and is able to release significant quantities of active agent in a prolonged and controlled manner. The objective of this invention is to provide a novel device that fulfills these requirements.

DISCLOSURE OF THE INVENTION

The invention is an inflatable device which is introduced into the lumen of the stomach, and inflated while in the stomach in order to prevent it from progressing into the lower gastrointestinal tract. A beneficial agent-containing cartridge is carried by the device and releases the agent to the stomach or the intestinal tract. The device may include means by which it may be retrieved from the stomach.

Accordingly, the invention is a removable inflatable intragastrointestinal beneficial agent delivery device adapted to reside within a stomach comprising:

(a) an inflatable member which is sized and shaped to pass through the esophagus in its deflated state and reside within the stomach and not pass through the pyloric sphincter in its inflated state;

(b) a hollow inflation tube for inflating the inflatable member one end of which is operably connected to the inflatable member and the other end of which carries a valve, said inflation tube having a length sufficient to extend from the mouth through the esophagus and into the stomach, providing a means by which the inflatable member may be inflated from outside the body with an inflation medium, and being adapted to reside within the stomach after the inflatable member is inflated; and (c) at least one cartridge member carried on the exterior of the inflatable member and/or the inflation tube, said member containing a beneficial agent and being capable of releasing said agent into the gastrointestinal tract.

The invention thus provides a removable platform from which drugs or other beneficial agents may be released into the gastrointestinal tract at predetermined doses and dosage regimens. The cartridge element(s) of the device is capable of receiving and holding unit doses of the agent, thus facilitating tailoring the dose, and/or dosage regimen or the administration of a multiplicity of different agents simultaneously or in a predetermined sequence. Further, the cartridge may be designed so that the unit doses can be removed and/or replaced, thus making it possible to alter or extend administration of the agent(s) at will.

BRIEF DESCRIPTION OF THE DRAWINGS

In the drawings, which are not to scale and in which like parts are referred to by the same reference numeral:

FIG. 1 is a partly sectional view of an embodiment of the device in its inflated state residing within the stomach.

FIG. 2 is a partly sectional view of the device of FIG. 1 in its deflated state being placed within the stomach via a naso-gastric tube.

FIG. 3 is a partly sectional view of the device of FIG. 1 in its inflated state and a syringe for inflating the device.

FIG. 4 is a sectional view of a beneficial agent-containing cartridge unit of the device of FIG. 1 taken along line 4—4 of FIG. 3.

FIG. 5 is a sectional view of another embodiment of the invention device where the cartridges reside within a cavity in the inflatable member of the device.

DETAILED DESCRIPTION OF EMBODIMENTS SHOWN IN DRAWINGS

The term "beneficial agents" as used herein is intended to include drugs, vitamins, and other chemicals or compositions that are administered gastrointestinally to humans or animals to achieve a beneficial effect on the recipient. The term "drug" as used herein broadly includes physiologically and/or pharmacologically active substances for producing a local effect within the gastrointestinal tract or a systemic effect at a remote site within the body.

FIGS. 1–4 depict an embodiment of the invention, generally designated 10. Device 10 is composed of three principal elements: an inflatable member 11, an inflation tube 12, and a plurality of beneficial agent-containing cartridges 13.

The inflatable member 11 is sized and shaped so that when deflated it can be inserted into the stomach 14 via a naso-gastric tube 15 (FIG. 2) that extends through the mouth 16 and esophagus 17 and opens into the stomach. Its size and shape in the inflated state (FIG. 1) are such that it resides comfortably within the stomach without being able to pass through the pyloric sphincter 18. While the inflated shape of member 11 is toroidal it will be appreciated that other shapes such as ovoidal, ellipsoidal, spheroidal, triangular, and the like may be employed. Shapes that have a central opening (such as a toroidal shape) allow stomach contents to pass through the pyloric sphincter even if the device settles against the pyloric region of the stomach. For human use the volume of the inflated member will normally be 20 to 1,000 cc, preferably 50 to 500 cc. Member 11 may be made solely of an elastomeric polymer or be an elastomeric laminated composite of metal foil, polymer or fiber.

Member 11 is inflated using hollow inflation tube 12, one end 18 (FIG. 3) of which operably connects into the lumen 19 of the inflatable member and the other end 20 of which carries a valve 21. The length of the tube is sufficient to extend through the mouth and esophagus and into the stomach with its end 20 outside the mouth. Valve 21 is designed to interconnect with a syringe 22 that may be charged with an inflation medium (either gas or liquid, preferably gas, and most preferably air).

Cartridges 13 are strung on inflation tube 12 in bead-like fashion. Referring to FIG. 4, each cartridge has an opening 23 through it that receives tube 12, thus enabling the cartridges to be so carried on the tube. It will be appreciated that the cartridges could interfit with, be carried by, or otherwise be affixed to the tube in other manners. As seen in FIG. 4 the cartridge may have a monolithic structure composed entirely of an agent (drug) formulation or agent dispersed in a matrix material. Alternatively, the cartridges may have a container structure composed of a housing or wall that defines a lumen and an agent formulation within the lumen. In container-type cartridges the wall may be agent-permeable, semipermeable, porous, or bioerodible, depending upon the nature of the agent release mechanism that is employed.

The structure and/or composition of the cartridge is preferably such that the release of agent from the cartridge will occur over a sustained period, e.g., from one day to one year. Various mechanisms to achieve sustained release such as diffusion, osmosis, bioerosion, swelling, dissolution or combinations thereof may be employed. Accordingly, in container-type cartridges the wall may have pores to permit gastric juice to enter the reservoir and contact the agent or agent-release mechanism within it. Alternatively, and depending upon the nature of the agent release mechanism, the wall may be required to be permeable to the agent or be semipermeable to permit gastric fluid to be imbibed into the pocket to effect agent release by an osmotic mechanism.

The agent may be in the form of a solid, gel, microcapsule, or liquid, depending, again, upon the nature of the cartridge and may be neat or formulated with carriers or diluents. It may be present in the form of a multiplicity of individual dosage units to facilitate tailoring of the dose. Alternatively, a multiplicity of different agents may be contained in the cartridges to achieve multi-agent administration simultaneously or in a predetermined sequence or pattern.

By using a multiplicity of unit dosage cartridges, doses may be easily adjusted via the number of cartridges. A cartridge may contain more than one agent or when more than one cartridge is employed the individual cartridges may contain different agents. The structure of the cartridge and/or the formulation of the agent within the cartridge are preferably such that the release of agent from the cartridge will be over a sustained time period.

FIG. 2 shows the manner in which device 10 is inserted into the stomach. The naso-gastric tube 15 is first inserted through the mouth and esophagus into the stomach. The device in its deflated state is then plunged down the tube 15 and into the stomach using a plunger 24. At this time, the valve end of the trailing inflation tube is left outside of the oral cavity. After the inflatable member has reached the stomach it is inflated with the desired inflation medium using a syringe or other inflation device. Once inflated, the size/shape of the inflatable member prevents the device from passing through the pyloric sphincter and entering the lower gastrointestinal tract. Finally, the inflation tube and valve are allowed to pass into the stomach. Then a fiberoptic gastroscope would be employed to ascertain the inflation and the gastric position of the device. Alternatively, the materials used to make the device may include a component that renders one or more elements of the device opaque to radiation, thereby permitting the device to be "seen" by conventional medical imaging devices.

The device may be left in the stomach from one day to one year for the sustained release of the agent from the cartridges.

The endoscopist may choose to add and/or remove beneficial agent cartridges once the device has been placed in the stomach. This could be achieved by retrieving the valve end of the tube magnetically using a magnetic ring 25 affixed to the valve end of the tube. After the endoscopist locates the valve, it would be magnetically retracted from the stomach, through the esophagus, with the trailing string of beneficial agent bearing cartridges. The addition or removal of cartridges could thus be performed.

Alternatively, the endoscopist may choose to leave the entire inflator valve and its trailing tubing in the stomach for the duration of the therapy, or use a heated endoscopic probe to heat-seal the tube at several points past the drug-bearing cartridges. Then the proximal section of the tube with its attached valve 21 could be cut and removed from the stomach by endoscopic forceps.

When the beneficial agent content of the device has been exhausted and/or if an early or temporary interruption of the administration is desired, the inflatable member could be either deflated or punctured endoscopically and recovered from the stomach by pulling it through the esophagus into the mouth with endoscopic forceps. An alternative recovery procedure would retrieve the valve end of the inflation tube magnetically and deflate the inflatable member with a syringe, thereby affording a smooth withdrawal of the entire device from the gastric lumen.

FIG. 5 depicts another embodiment of the invention device, generally designated 26. Device 26 differs from device 10 as regards the structure of the inflatable member and the manner in which the agent-containing cartridges are carried. Device 26 has an inflatable member 27 that is generally ellipsoidal in shape in its inflated state (shown in FIG. 5) and has an opening or channel 28 extending through it. Opening 28 defines a cavity in which cartridges 13 reside. The ends of the opening are closed by caps 29 which have perforations 30 to permit gastric fluids to flow into and through the opening, thereby contacting cartridges 13. In its deflated state (not shown) the profile of device 26 is essentially that of the cartridge-containing channel. Devices of such structure have the feature that the agent-containing capsules are kept from contacting the gastric mucosa directly. It should be noted that the cartridges are considered to be carried on the "exterior" of the inflatable member even though they are confined within channel 28. In this regard the term "exterior" intends any surface of the inflatable member that is capable of direct contact with gastric fluids when the device is in the stomach.

Other embodiments of the invention that are obvious to those of skill in the fields of drug delivery devices, endoscopy, or related fields are intended to be within the scope of the following claims.

We claim:

1. A removable inflatable intragastrointestinal beneficial agent delivery device adapted to reside within a stomach comprising:
    (a) an inflatable member which is sized and shaped to pass through the esophagus in its deflated state and reside within the stomach and not pass through the pyloric sphincter in its inflated state;
    (b) a hollow inflation tube for inflating the inflatable member once the inflatable member is within the stomach, one end of which is operably connected to the inflatable member and the other end of which carries a valve, said inflation tube having a length sufficient to extend from the mouth through the esophagus and into the stomach, providing a means by which the inflatable member may be inflated from outside the body and being adapted to reside within the stomach after the inflatable member is inflated;
    (c) at least one cartridge member carried on the exterior of the inflatable member and/or the inflation tube, said member containing a beneficial agent and being capable of releasing said agent into the gastrointestinal tract.

2. The device of claim 1 wherein the beneficial agent is a drug.

3. A removable inflatable intragastrointestinal beneficial agent delivery device adapted to reside within a stomach comprising:
    (a) an inflatable member which is sized and shaped to pass through the esophagus in its deflated state and reside within the stomach and not pass through the pyloric sphincter in its inflated state;
    (b) a hollow inflation tube for inflating the inflatable member once the inflatable member is within the stomach, one end of which is operably connected to the inflatable member and the other end of which carries a valve, said inflation tube having a length sufficient to extend from the mouth through the esophagus and into the stomach, providing a means by which the inflatable member may be inflated from outside the body and being adapted to reside within the stomach after the inflatable member is inflated;
    (c) at least one cartridge member carried on the exterior of the inflatable member and/or the inflation tube, said cartridge member containing a beneficial agent and being capable of releasing said agent into the gastrointestinal tract, and
    (d) a magnetic body carried proximate to said other end of the inflation tube and providing a means by which the inflation tube may be magnetically retrieved from the stomach via the esophagus and mouth.

4. A removable inflatable intragastrointestinal beneficial agent delivery device adapted to reside within a stomach comprising:
   (a) an inflatable member which is sized and shaped to pass through the esophagus in its deflated state and reside within the stomach and not pass through the pyloric sphincter in its inflated state;
   (b) a hollow inflation tube for inflating the inflatable member once the inflatable member is within the stomach, one end of which is operably connected to the inflatable member and the other end of which carries a valve, said inflation tube having a length sufficient to extend from the mouth through the esophagus and into the stomach, providing a means by which the inflatable member may be inflated from outside the body and being adapted to reside within the stomach after the inflatable member is inflated; and
   (c) at least one cartridge member carried on the exterior of the inflation tube, said cartidge member containing a beneficial agent and being capable of releasing said agent into the gastrointestinal tract and having an opening through it and being strung on the inflation tube via the opening.

5. The device of claim 4 wherein there is a plurality of cartridges, each of which has an opening through it, said cartridges being strung on the inflation tube via the openings.

6. A removable inflatable intragastrointestinal beneficial agent delivery device adapted to reside within a stomach comprising:
   (a) an inflatable member which is sized and shaped to pass through the esophagus in its deflated state and reside within the stomach and not pass through the pyloric sphincter in its inflated state said inflatable member having an opening in it that defines a cavity;
   (b) a hollow inflation tube for inflating the inflatable member once the inflatable member is within the stomach, one end of which is operably connected to the inflatable member and the other end of which carries a valve, said inflation tube having a length sufficient to extend from the mouth through the esophagus and into the stomach, providing a means by which the inflatable member may be inflated from outside the body and being adapted to reside within the stomach after the inflatable member is inflated; and
   (c) at least one cartridge member carried in the cavity of the inflatable member, said cartridge member containing a beneficial agent and being capable of releasing said agent into the gastrointestinal tract.

7. The device of claim 6 wherein the ends of the opening are closed by perforated members.

8. The device of claim 6 wherein there is a plurality of cartridges each of which resides in the cavity.

9. The device of claim 1 wherein the inflatable member has a toroidal shape in its inflated state.

* * * * *